(12) United States Patent
Kaiser et al.

(10) Patent No.: US 8,969,283 B2
(45) Date of Patent: Mar. 3, 2015

(54) LOW ODOR, HARD SURFACE SPORICIDES AND CHEMICAL DECONTAMINANTS

(75) Inventors: Herbert J. Kaiser, Pontoon Beach, IL (US); Bryan M. Tienes, Boulder, CO (US)

(73) Assignee: American Sterilizer Company, Mentor, OH (US)

( * ) Notice: Subject to any disclaimer, the term of this patent is extended or adjusted under 35 U.S.C. 154(b) by 674 days.

(21) Appl. No.: 12/658,234

(22) Filed: Feb. 4, 2010

(65) Prior Publication Data

US 2010/0196505 A1 Aug. 5, 2010

Related U.S. Application Data

(63) Continuation-in-part of application No. 12/322,702, filed on Feb. 5, 2009.

(51) Int. Cl.
| | | |
|---|---|---|
| C11D 7/18 | (2006.01) | |
| C11D 3/39 | (2006.01) | |
| A01N 37/16 | (2006.01) | |
| A01N 59/00 | (2006.01) | |
| C11D 3/30 | (2006.01) | |
| C11D 3/48 | (2006.01) | |
| C11D 3/33 | (2006.01) | |
| C11D 17/00 | (2006.01) | |

(52) U.S. Cl.
CPC .............. *C11D 3/3947* (2013.01); *A01N 37/16* (2013.01); *A01N 59/00* (2013.01); *C11D 3/30* (2013.01); *C11D 3/48* (2013.01); *C11D 3/33* (2013.01); *C11D 17/0013* (2013.01)
USPC ........... 510/375; 510/108; 510/372; 510/382; 510/445; 568/568

(58) Field of Classification Search
USPC ........... 510/108, 372, 375, 382, 445; 568/568
See application file for complete search history.

(56) References Cited

U.S. PATENT DOCUMENTS

| | | | | |
|---|---|---|---|---|
| 3,148,018 A | * | 9/1964 | Easton et al. | 8/111 |
| 3,839,234 A | * | 10/1974 | Roscoe | 510/435 |
| 4,497,725 A | * | 2/1985 | Smith et al. | 8/137 |
| 4,722,413 A | * | 2/1988 | Okubo | 180/247 |
| 4,772,413 A | | 9/1988 | Massaux et al. | |
| 5,350,563 A | | 9/1994 | Kralovic et al. | |
| 5,977,053 A | | 11/1999 | Groth et al. | |
| 6,251,845 B1 | | 6/2001 | Herbots et al. | |
| 6,514,509 B2 | | 2/2003 | Tabasso | |
| 7,235,252 B2 | | 6/2007 | Preto et al. | |
| 2004/0127381 A1 | * | 7/2004 | Scialla et al. | 510/372 |
| 2005/0058719 A1 | * | 3/2005 | Ramirez et al. | 424/616 |

FOREIGN PATENT DOCUMENTS

| | | |
|---|---|---|
| EP | 0 598 170 A1 | 2/1998 |
| GB | 907356 | * 10/1962 |

* cited by examiner

*Primary Examiner* — Ali Soroush
(74) *Attorney, Agent, or Firm* — Hudak, Shunk & Farine Co. LPA (57) ABSTRACT

A low odor, liquid disinfectant composition comprising multiple components, which, upon mixing, provide an aqueous solution comprising low levels of peracetic acid for use in decontaminating articles and surfaces contaminated with bacteria, viruses, fungi and other chemical and biological contaminants including, but not limited to, spores, such as *Clostridium difficile* (*C. diff*), *Clostridium sporogenes*, and anthrax, mouse parvo virus, and mustard, nerve and other chemical and biological warfare agents. The disinfectant composition is prepared just prior to use by combining two or more separately packaged components, one component which is an acetyl donor comprising TAED or DAMA, and the other component which is a hydrogen peroxide solution.

10 Claims, 7 Drawing Sheets

LOW ODOR, HARD SURFACE SPORICIDES AND CHEMICAL DECONTAMINANTS

CROSS REFERENCE

This application is a continuation-in-part of U.S. application Ser. No. 12/322,702, filed Feb. 5, 2009 entitled "Low Odor, Hard Surface Sporicide", herein fully incorporated by reference.

The U.S. Government may have certain rights in this invention under the ECBC Contract No. W911 SR-06-C-0048.

FIELD OF THE INVENTION

This invention is directed to a low odor, liquid decontamination/disinfectant composition comprising multiple components, which, upon mixing, provide an aqueous solution comprising low levels of peracetic acid for use in decontaminating articles and surfaces contaminated with bacteria, viruses, fungi, and other chemical or biological contaminants or warfare agents, including, but not limited to, spores such as *Clostridium difficile* (*C. diff*), *Clostridium sporogenes* and anthrax, mouse parvo virus, and mustard, nerve and other chemical and biological warfare agents. The inventive compositions are prepared just prior to use by combining two or more separately packaged components.

BACKGROUND OF THE INVENTION

Recently, there has been a high interest in environmental sporicides due to threats posed by, among other things, anthrax as a biological warfare agent, *C. diff* epidemics in hospitals, and mouse parvo virus in animal labs. There is significant interest in the critical environment markets, such as hospitals, laboratories, clinics, and research and manufacturing facilities, for a product with improved sporicidal efficacy that can be used to disinfect, sterilize and decontaminate hard surfaces. There is also significant interest in cleaning and decontaminating surfaces contaminated with chemical and other biological warfare agents in a wide variety of settings.

Hospital-acquired infections linked to exposure to *C. diff* spores are a universal health-care crisis. Infection with *C. diff* is life-threatening to many patient populations, and contamination of equipment, materials, and surfaces with spores produced by *C. diff* bacteria occurs frequently, despite the best efforts at infection control. Part of the reason is that *C. diff* spores can survive on surfaces for long periods and are inherently difficult to destroy. Diligent efforts are necessary to eradicate the spores and require the use of disinfectant cleaning compositions with efficacy against spores and bacteria that produce them.

Similarly, in the pharmaceutical industry, manufacturing facilities have experienced a number of product recalls and plant shutdowns due to contamination with bacteria, viruses, fungi, spores (including spore-forming bacteria) and other biological contaminants. There has been an increase in the use of disinfectant sterilant products for cleaning pharmaceutical manufacturing equipment and surfaces.

The main products used in the cleaning and disinfection of surfaces contaminated with biological materials, specifically spores, are predominately oxidizing compositions, such as liquid or granular hypochlorite solutions (bleach), or hydrogen peroxide-based products such as East Decon™ developed by Sandia National Laboratories. Specific to *C. diff*, the standard practice in most health care institutions is to use a product based upon sodium hypochlorite, also known as bleach. Hypochlorite-based disinfectants have been used with some success for surface disinfection in those patient-care areas where surveillance and epidemiology indicate ongoing transmission of *C. diff*. At present, there are no EPA-registered products with specific claims for inactivating *C. diff* spores, but there are a number of registered products that contain hypochlorite. As discussed below, while achieving efficacy in eradication of spores, use of currently available "bleach" products has many drawbacks.

Products used in the pharmaceutical manufacturing industry to eradicate spores and spore-forming bacteria rely on oxidizing chemistries, one of which is hydrogen peroxide. Like the use of hypochlorite-based products in health care institutions, the use of hydrogen peroxide chemistries for bacterial eradication in the pharmaceutical industry also suffers from many disadvantages.

Many sporicide products are available commercially. In addition to hypochlorite and hydrogen peroxide, products containing alcohols, peracetic acid (PAA), peracetic acid in combination with alcohols, hypochlorite or peroxide, and various products that utilize peroxygen sources and acetyl donors to generate both peracetic acid and hydrogen peroxide, are available as disinfectants or sterilants. These commercially available products, while effective in part, have some disadvantages.

Many of these products have aesthetic and handling disadvantages, such as harshness (acidity or alkalinity), strong odor, and skin and mucous membrane irritation, due to high concentrations of active components. Most currently available products require overly cumbersome personal protective equipment to be used during their application to limit exposure, thus adding to their costs. The use, storage and transportation of these known, decontamination products thus present significant physical and health hazards and logistical challenges in shipping, handling and storage.

In particular with regard to spores, alcohol-based disinfectants, alone, are not effective against *C. diff* or other spores, or spore-forming bacteria. Nor is liquid hydrogen peroxide alone effective against spores or other biological contaminants without additives to boost its reactivity.

Hypochlorite bleach, although efficacious against *C. diff*, is not without the aforenoted disadvantages. In addition, sodium hypochlorite has poor materials compatibility. Most sodium hypochlorite products are alkaline in nature and are corrosive to many materials, such as stainless steel, brass and copper. In addition, it has been shown that sodium hypochlorite can "strip away" waxes commonly used on hospital surfaces, making it an impractical choice for mopping applications. Further, sodium hypochlorite is associated with a difficult-to-rinse residue, which may contribute to its "stripping" effect. Finally, sodium hypochlorite demonstrates only moderate efficacy against certain organisms. It degrades rapidly in the presence of an organic soil load, thus negatively impacting its efficacy.

Handling requirements also need to be considered. Oxidizing chemistries, such as bleach and hydrogen peroxide formulations, are also known to be harsh chemistries requiring specific handling requirements. Depending on concentration, hydrogen peroxide may be subject to stringent handling restrictions. It may also be associated with strong odors and inhalation irritation issues. The OSHA permissible exposure limit (PEL) is 1 ppm for hydrogen peroxide. Some combination products, containing hydrogen peroxide as one component, may still be subject to air shipment restrictions based upon the concentration of hydrogen peroxide. In most cases, the products need to be shipped either by ground or sea causing delays in their arrival at required locations. Air shipment is possible for hydrogen peroxide, but quantities are severely limited and require special packaging.

Both sodium hypochlorite and hydrogen peroxide in high concentrations are corrosive to metal substrates, require special packaging, have limited transportation modalities and unstable without controlled transportation systems. Storage is also problematic. The storage of large amounts of highly corrosive and heat sensitive liquids is a safety issue. Bleach (hypochlorite) decomposes quickly at high temperatures resulting in a significant loss of efficacy and, therefore, has limited shelf life. Hydrogen peroxide spontaneously and irreversibly decomposes at elevated temperatures. Both hypochlorite- and hydrogen peroxide-based materials will also decompose rapidly when subjected to environmental contaminants such as dirt or blowing sand.

It is further noted that in addition to metal substrates, bleach and hydrogen peroxide are incompatible with a number of non-metal substrates such as paints, soft metals, rubbers and plastics.

Similarly, peracetic acid can achieve a high level of decontamination, disinfection and sterilization against both biological and chemical contaminants; however, concentrated solutions of peracetic acid are corrosive and are strong oxidizers. Strong oxidizers are expensive to ship and handle. They also present a safety hazard for customers in use, as well as during packaging. Typically, liquid peracetic acid is extremely unstable and must be separated from the rest of the formula in the product package. Even with separate packaging, products containing peracetic acid tend to have a limited shelf life.

Generating peracetic acid in situ from a solid acetyl donor may solve certain shipping, handling and stability problems. Typically, in systems that generate peracetic acid in situ, the peroxide source is also a solid persalt, such as sodium percarbonate or sodium perborate. While these products have longer shelf life and a good safety profile, they are often cumbersome to dissolve and require extended periods of time to generate effective concentrations of peracetic acid. Due to the typically high solids content of the resulting solutions of these products, there is the potential of leaving substantial residues on surfaces. These residues need to be rinsed or wiped from the surface. This is a particular disadvantage with respect to chemical and biological warfare agent decontamination, which is likely to be encountered in situations and areas where adequate rinse water supply is not readily available.

Finally, another disadvantage of most commercially available hydrogen peroxide and peracetic acid systems is that they cannot be sold as sterile. In order to create sterile products, the systems must be capable of being sterilized with gamma-irradiation. Gamma irradiation is commonly used in the pharmaceutical industry to sterilize cleaning compositions. Most commercial peracetic acid and hydrogen peroxide systems are not stable when exposed to gamma-irradiation and cannot be sterilized in this manner, requiring additional sterilization steps, if a sterile product is needed, adding to the costs associated with their use.

Accordingly, in the health care market and the pharmaceutical industry, an effective sporicide with EPA-approved claims against *C. diff* is needed to address the emerging health care and product contamination issues. *C. diff* spores can live on surfaces for years. *C. diff* spores are very difficult to kill. As mentioned above, sporicide products are available, but most have safety, odor, material compatibility and handling issues, among others. Currently, there are no EPA-approved products to address *C. diff* spores. The current practice in most health care institutions is to use a 10% solution of hypochlorite to clean all articles presumed to be contaminated with *C. diff* spores. There is a need, therefore, for a product having lower odor, better materials compatibility, improved safety profile, less stringent shipping requirements, and less onerous handling and storage parameters than currently existing products.

Formulations comprising peracetic acid, or components capable of generating peracetic acid (PAA) in situ, are effective sporicides and are nearly equivalent to acidified bleach, an industry standard for efficacy against spores. A new sporicide system for each of the above-discussed markets (health care and pharmaceutical manufacturing) has been developed, having unexpected efficacy against spores and spore-forming bacteria, such as *C. diff*, as well as other bacteria, virus, or fungi, but without the disadvantages of currently available products. The new inventive systems comprise formulations that also have excellent activity in decontaminating surfaces exposed to chemical and biological warfare agents. Different embodiments of these inventive systems may be used depending on the needs of the market served; however, the foundation of the chemistry is the same: generation of peracetic acid through the perhydrolysis of an acetyl donor, such as tetraacetylethylenediamine (TAED) or diacetylmethylamine (DAMA) in combination with a hydrogen peroxide solution.

Product formulations containing peracetic and/or components for generating peracetic acid are known in the art. Peracetic acid is supplied typically as a concentrated or diluted solution, or is generated in situ from an acetyl donor and a peroxide source. Systems comprising dry components exist that utilize solid peroxygen sources and acetyl donors, which, when mixed with water, produce peracetic acid (PAA). (See e.g., U.S. Pat. No. 5,350,563, directed to a two-part perborate/acetyl donor powdered formulation.) While dry product forms have application in certain cases and have an advantage of a longer shelf life and good safety profile, they are generally limited by slow generation of PAA at room temperature and, therefore, there is a preference for more rapid acting liquid products in certain applications. Use of dry peroxygen components is disadvantageous due to the time needed to generate hydrogen peroxide before activation (combination) with the acetyl donor. A particular disadvantage to multi-component dry systems is that the components dissolve very slowly in water, such that the desired concentration of active ingredients is not fully available until later stages. There is also an additional risk that undissolved components will remain and not be rinsed away. On the other hand, a system or formulation utilizing a liquid hydrogen peroxide component has been found to generate PAA much faster as the perhydroxyl ion is available immediately upon combination with an acetyl donor, regardless of whether the acetyl donor is in solid or liquid form.

Other liquid commercial products containing both peracetic acid and hydrogen peroxide are also known. For example, a liquid product produced by Decon Labs, known as "SporGon" comprises 7.35% hydrogen peroxide and 0.23% peracetic acid; however, the high level of hydrogen peroxide in use requires a limitation of exposure. OSHA limits personal hydrogen peroxide exposure to 1 ppm. In addition, the product requires at least three hours to achieve sterilization. Another example is Oxonia Active, an acidic liquid sanitizer, produced by Ecolab. This product is highly corrosive and has a hydrogen peroxide level of 27.5% and peracetic acid level of 5.8%. The high level of hydrogen peroxide requires, in addition to exposure limits, stringent shipping and handling requirements. In most instances, these products cannot be gamma-irradiated, the preferred method for sterilization of pharmaceutical industry disinfectants.

Liquid systems for generating PAA are also known. By way of example, U.S. Pat. Nos. 6,514,509 and 7,235,252 are directed to systems for preparing organic peroxy acids using a parent solution and activator and requiring a hydroalcoholic environment (at least 10% alcohol) with an acid pH. The alcohol purportedly acts as an additional germicide. In contrast, the present invention does not utilize or require a hydroalcoholic environment and does not utilize strong inorganic acids to maintain an acid pH. Importantly, peracetic acid is generated in an alkaline environment, not acidic, and the resulting product rapidly converts to a neutral pH upon peracetic acid generation. There is no need for an additional germicide.

European Patent 0 598 170 B1 is a cleaning composition based on hydrogen peroxide (or a peroxygen source) combined with acetyl triethyl citrate as a bleach activator. The bleach activator requires emulsification with at least two surfactants having different HLB values. The components are all combined in one unitary liquid composition.

The present invention is based upon combining an acetyl donor, alkalinity agents and a liquid hydrogen peroxide source to produce an effective concentration of peracetic acid in situ to destroy C. diff spores. The components of the present invention are separately packaged and, thus, the formulation is "ready-to-use" upon activation (combination of ingredients) and requires no further dilution or manipulation of components. Generation of peracetic acid is much faster due to the immediate availability of the perhydroxyl ion, as liquid hydrogen peroxide, as compared to products using a dry peroxygen source. Surprisingly, the present formulations are effective at much lower concentrations of peracetic acid than currently available products.

The present invention provides sporicidal formulations having a pH in the neutral range (4-8), which allows for easier disposal versus highly alkaline or acidic products, and has superior materials compatibility against soft metals, plastics, resins and other materials, as compared to bleach. The inventive formulations also result in low odor products that are less caustic or irritating to personnel than existing products, including those containing higher levels of peracetic acid, and may eliminate the need for respiratory protection required for application of higher concentrations of PAA and acidified bleach. They have no detectable levels of acetic acid or hydrogen peroxide. Most commercially available PAA-containing products require the use of acetic acid to stabilize the peracetic acid for longer shelf life, greatly increasing the odor profile. Since peracetic acid is generated in situ with the present invention, there is no need for the addition of acetic acid or any other acid, thus reducing or eliminating the odor profile.

The present invention also provides for no-rinse decontamination, thus allowing for an effective decontamination where rinse water is not readily available and/or reducing the amount of water required for standard decontamination by about 50%. This is especially advantageous in decontamination of chemical and biological warfare agents, which may be encountered in a wide variety of environments.

Unexpectedly, the formulations of the present inventions are efficacious against a wide range of bacteria, viruses, fungi and spores, including C. diff, as well as against several chemical and biological warfare agents, without the addition of additional decontaminants, disinfectants, biocides or germicides and, hence, are less costly. Microbial efficacy has been shown even in the presence of an organic soil load and at a lower concentration of peracetic acid. Surfactants utilized in the present system are excellent cleaners, improving efficacy in the presence of an organic soil. Finally, the inventive formulations comprise low levels of hydrogen peroxide, which is not subject to stringent shipping and handling requirements.

Other advantages of the present invention include increased shelf life of peracetic acid-based disinfectants, improved dissolution and mixing time, and increased pot life.

Tetraacetylethylenediamine (TAED) is the preferred acetyl donor for the present invention; however, diacetylmethylamine (DAMA) also yields comparable results and, indeed, may be preferred in chemical and biological warfare agent decontamination. Hydrogen peroxide is the chosen perhydroxyl source. Hydrogen peroxide may be used either as a formulation comprising hydrogen peroxide, surfactants and fragrance, or alternatively, as a plain aqueous solution. Both TAED and hydrogen peroxide are currently registered EPA-active ingredients. DAMA is not an EPA registered active ingredient, but is available in a clear liquid form at room temperature and provides rapid PAA generation and immediately clear, low-residue end-use solutions.

While several different embodiments are contemplated for the inventive formulations, they all share the advantageous properties of preparation at a neutral pH, low odor, better materials compatibility, improved safety profile and high efficacy.

In one embodiment, a two-part system comprises a solid, dry TAED powder activator and a formulated hydrogen peroxide solution comprising hydrogen peroxide, a surfactant and a fragrance.

In another embodiment, a three-part liquid system comprises first, a two-part liquid TAED activator (comprising in two parts, a separate TAED suspension and a separate alkaline liquid solution) and, as the third part, the same formulated hydrogen peroxide as used in the two-part system above.

In yet another embodiment, a two-part liquid system comprises a first solution containing an acetyl donor (in liquid form or combined with a solvent) and a second solution comprising aqueous hydrogen peroxide. An amine alkalinity source could be a third component or be included with the acetyl donor portion in this embodiment.

All embodiments, upon activation (combination), generate lower levels of peracetic acid with unexpected anti-microbial and decontaminating efficacy.

It is an object of this invention to provide a low odor disinfectant having efficacy against bacteria, viruses, fungi and other biological materials, including spores and spore-forming bacteria, such as C. diff, as well as chemical and biological warfare agents.

It is a further object of this invention to provide a low-odor peracetic acid solution with greatly improved safety and handling features over currently available products.

Still a further object of this invention is to provide a system for rapid generation of peracetic acid in an alkaline pH environment, which quickly drops into the neutral range upon peracetic acid generation, resulting in a product that is usable within a short period of time after combination and having a use life of at least 24 hours.

Yet a further object of this invention is to provide a peracetic acid solution which has efficacy even in the presence of an organic soil load.

It is a further object of this invention to provide an effective, safer alternative to hypochlorite or other oxidizing chemistries for use in health care environments to eradicate C. diff spores.

Finally, it is an object of this invention to provide a "no rinse" peracetic acid cleaner and/or a peracetic acid that requires no, or less, rinse water for removal as compared to conventional products currently available.

These and other objects of the invention will be apparent based upon the description herein.

SUMMARY OF THE INVENTION

The invention is directed to a low-odor sporicide/decontaminant based upon the generation of peracetic acid from an acetyl donor combined with liquid hydrogen peroxide. The peracetic acid is generated in an alkaline environment, and the final product has a neutral pH, making it safer and easier to handle and transport. The liquid hydrogen peroxide component allows for rapid generation of peracetic acid compared to conventional products based upon dry peroxygen sources. Surprisingly, the low levels of peracetic acid generated are effective against bacteria, viruses, fungi and other microbes, including spore formers, such as C. diff, as well as chemical or biological warfare agents, without the need for high concentrations of peracetic acid or the addition of other disinfectant or sterilizing agents.

In one embodiment, the inventive composition comprises:
 a) a solid activator blend comprising a solid acetyl donor combined with a solid alkalinity source; and
 b) a hydrogen peroxide solution,
 wherein the solid activator blend is mixed with the hydrogen peroxide solution just prior to use to form a peracetic acid solution.

In a second embodiment, the inventive composition comprises:
 a) a two-part liquid activator comprising in one part, an acetyl donor dispersion, and in the other part, an alkaline solution; and
 b) a hydrogen peroxide solution,
 wherein the acetyl donor dispersion and alkaline solution are mixed with the hydrogen peroxide solution just prior to use to form peracetic acid.

In a third embodiment, the inventive composition comprises:
 a) a liquid comprising an acetyl donor in a solvent;
 b) a hydrogen peroxide solution;
 c) an alkalinity source as a third component, or as a part of the acetyl donor liquid to catalyze a peracetic acid generating reaction, and
 d) optionally, a surfactant;
 wherein the acetyl donor containing liquid is mixed with the hydrogen peroxide solution just prior to use and reacts to form a peracetic acid solution.

In some embodiments, the hydrogen peroxide solution may be formulated with a surfactant, fragrance, and water. Alternatively, a dilute, aqueous solution of hydrogen peroxide may be used. Optionally, surfactants may be contained within the acetyl donor component.

In all embodiments, hydrogen peroxide is used in very low amounts, preferably less than 8 to about 10 weight percent, more preferably less than 3 weight percent, and most preferably less than 1.5 weight percent. The lower concentration of hydrogen peroxide avoids shipping and handling restrictions and is safer for use. Once mixed, the hydrogen peroxide content remains close to the original low levels that were present prior to mixing.

The concentration of peracetic acid produced can vary depending on the amounts of activator (acetyl donor portion) and hydrogen peroxide solution that are combined.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

The general chemistry that forms the base of the claimed compositions is peracetic acid, generated from the combination of an acetyl donor, such as TAED or DAMA, and hydrogen peroxide at an alkaline pH, as the source of antimicrobial efficacy. Both TAED and hydrogen peroxide are recognized by the EPA as active ingredients. DAMA is not. The claimed compositions utilize components that are kept separate until such time as the disinfectant solution is needed. Once mixed, the compositions have a use life of about 24 hours. Typically, the claimed compositions generate from about 0.05 to about 0.25% peracetic acid solutions, but concentrations may vary depending on the amount of acetyl donor utilized and may range up to about 2.5%.

As one component, the inventive compositions comprise an acetyl donor, such as TAED or DAMA. Typical acetyl donors would be of the form presented in Formula 1 below.

Basic structure of the acetyl donor.

Formula 1.

wherein $R^1$, $R^2$ and $R^3$ could be any group which would not interfere with the generation of peracetic acid, would not be oxidized in the system, and would allow for the dissolution of the acetyl donor.

In a first embodiment, the activator is in solid powder or "dry" form. TAED is the preferred acetyl donor. Solid TAED is first coated with a surfactant or blend of surfactants to aid in dissolution upon activation. The surfactant used to coat the TAED is typically anionic, although the claimed compositions are not limited to anionic surfactants. One useful surfactant is alkyldiphenyl oxide disulfonate, sold as an aqueous 45% active solution under the name Dowfax C10-L. Other anionic surfactants useful in the present invention include N-oleoyl sarcosinate and dodecylbenzene sulfonic acid.

The surfactant is applied to the TAED as an aqueous solution, wherein the TAED, traditionally water insoluble, is mixed into a slurry. The slurry is then dried, and the resulting "cake" is pulverized into a powder, which is comprised of TAED coated with a surfactant. This "coated" TAED is then blended with two dry alkalinity sources. The complete blend of the "coated" TAED with the dry alkalinity sources comprises the dry "activator" portion of the composition. In this embodiment, the alkalinity sources for the powdered, coated TAED include sodium carbonate and a biodegradable chelating agent such as the tetrasodium salt of iminodisuccinic acid (sold under the trade name Baypure CX 100). Advantageously, the iminodisuccinic acid also acts as a chelating agent which aids in the efficacy of the system in the presence of an organic load.

At the time of, or just prior to, use, the dry "activator" is combined with a formulated hydrogen peroxide solution, which contains hydrogen peroxide and a surfactant or blend of surfactants. A formulation of liquid hydrogen peroxide is preferred over a dry perhydroxyl or peroxygen source due to much faster generation of peracetic acid achieved upon combination of the liquid hydrogen peroxide with the TAED activator. When combined (or "activated"), peracetic acid is generated. Depending on the amounts of activator and hydrogen peroxide selected, various concentrations of peracetic acid may be generated. Upon activation, the product, regardless of PAA concentration, will have a 24-hour pot-life (i.e., "shelf" or "use-dilution" life).

In a second embodiment, the acetyl donor, i.e., "TAED activator", is itself a two-part liquid activator system. As one part of the liquid activator, a TAED dispersion is prepared. TAED is suspended in an aqueous system that includes a suspending agent, and perhaps surfactants and solvents. Typical suspending agents include magnesium aluminum silicate and Xanthan gum. The second part of the liquid activator is an alkaline, aqueous solution comprising an alkalinity source and surfactant(s). The alkalinity source can be a hydroxide, amine or chelating agent, or combinations thereof. Typical examples include sodium hydroxide, monoethanol-amine, triethanolamine, 2-amino-2-methyl-1-propanol, and other amines.

For the embodiment utilizing a two-part liquid TAED activator, anionic or nonionic surfactants may be used. Typical anionic surfactants include N-oleoyl sarcosinate, alkyldiphenyloxide disulfonate, and dodecylbenzene sulfonic acid. A typical nonionic surfactant is polyoxyethylene sorbitan monolaurate. Other useful surfactants are known to those skilled in the art.

Each part of the "two-part liquid TAED activator" system is kept physically separated (through packaging). Just prior to use, both parts are added to the formulated hydrogen peroxide solution, and peracetic acid is generated. The concentration of peracetic acid generated depends on the quantities of activator and hydrogen peroxide selected. Again, this product, upon activation, will have a 24-hour pot-life.

In both the first and second embodiments, the "activator" portions (dry, coated TAED in the first embodiment or two-part liquid TAED/alkaline solution in the second embodiment) are mixed with a specifically-formulated liquid hydrogen peroxide solution, which contains a surfactant to aid both in wetting of the product in use and controlling the foam profile on activation. Useful surfactants for the hydrogen peroxide solution can be anionic, nonionic or amphoteric in nature. Typical examples are sodium lauryl sulfate, sodium octyl sulfate, Dowfax C10-L, and Pluronic F-127. Other useful surfactants are known to those skilled in the art. Generally, non-foaming or low-foaming surfactants are preferred. The hydrogen peroxide solution may also contain a fragrance to provide a pleasing odor. The amount of hydrogen peroxide in the formulation may be as high as 10%; however, optimally it is less than about 8% but greater than 0.1%, and most preferably less than 5% but greater than 0.50%.

The pH of the hydrogen peroxide solution is about 4.5, and the pH of the inventive composition is neutral (4-8).

In a third embodiment, DAMA is the preferred acetyl donor, although TAED has been shown to be effective. A first part or portion comprising DAMA, an optional surfactant and a solvent is prepared as a separate solution. This first part is mixed with a hydrogen peroxide solution at the time of use. An amine alkalinity source is added as either a third component or included in the acetyl donor (first) solution. If liquid DAMA is used, the solvent may be omitted.

The components are packaged separately and mixed by the consumer just prior to use. The result of mixing is rapid generation of peracetic acid in situ according to the reaction scheme shown in Formula 2 below:

The solvent and surfactants, when used, act as wetting and cleaning agents on hard surfaces. The solvent also aids in the dissolution of chemical warfare agents and increases the evaporation rate from surfaces. The peracetic acid resulting from the reaction is capable of rapidly disinfecting and decontaminating surfaces. After application to the surface, the solution evaporates from the surface with very little residue and does not need to be rinsed.

Other known acetyl donors useful in the inventive compositions may include aspirin (acetylsalicylic acid), n-methyl diacetamide, and triacetin; however, TAED and DAMA are preferred.

TAED is present in the dry activator portion of the first embodiment in amounts ranging from about 40 to about 75 weight percent, based upon the weight of the dry activator component. TAED is present in the TAED dispersion portion (activator) of the second embodiment in amounts ranging from about 30 to about 40 weight percent, based upon the weight of the TAED dispersion. Generally, one mole of TAED generates two moles of peracetic acid, but the concentration of peracetic acid generated will depend on the amounts of activator and hydrogen peroxide that are combined.

DAMA is present in the acetyl donor portion of the third embodiment in amounts ranging from about 0.5 to about 10 weight percent, based upon the total weight of the combined components (parts), i.e., use dilution.

Surfactants useful in the present inventions include alkyldiphenyl oxide disulfonate (Dowfax C10-L), N-oleoyl sarcosinate, dodecylbenzene sulfonic acid, sodium lauryl sarcosinate and Tergitol L-62 (an ethylene oxide/propylene oxide co-polymer).

Surfactants that have a tendency to create excessive foam during mixing are less preferred over foam-reducing surfactants. Surfactants are important in the decontamination process for chemical agents, since they achieve the desired solubility of the chemical agent without negative ramifications. Surfactants also improve wetting features and can reduce the appearance of residues on a surface.

Surfactants are present in the "dry activator portion" of the first embodiment in amounts ranging from about 5 to about 20 weight percent, based on the weight of the dry activator portion.

Surfactants are present in the TAED dispersion portion of the two-part liquid activator of the second embodiment in amounts ranging from about 0.5 to about 5 weight percent, based upon the weight of the TAED dispersion. Surfactants are present in the alkaline solution portion of the two-part activator system in amounts ranging from about 0 to about 10 weight percent, based upon the weight of the alkaline solution.

Optional surfactants, if present in the third embodiment, range in amounts from about 0.03 to about 5 weight percent, based upon the total weight of the combined components (parts), i.e., use dilution.

Finally, surfactants may be present in the formulated hydrogen peroxide solution in amounts ranging from about 0.01 to about 2 weight percent, based upon the total weight of the formulated hydrogen peroxide solution.

Various alkalinity sources and buffers are also used in the claimed compositions. Exemplary alkalinity sources for a "dry" TAED activator include sodium carbonate. Glycolic acid is an example of a buffer for the TAED dispersion. These examples are not intended to be limiting, as buffers are known to those skilled in the art. Iminodisuccinic acid derivatives are also useful as alkalinity agents in both the dry TAED activator and the two-part liquid TAED/alkaline solution activator and also function as chelating agent(s). 2-amino-2-methyl-1 propanol (AMP 95) also serves as a useful alkalinity source and solvent.

The alkalinity source for the DAMA-based system preferably comprises a primary, secondary or tertiary amine. Amine-based alkalinity sources act to catalyze the peracetic acid generating reaction. Requirements for the amine are a pKa sufficiently high to catalyze the reaction and solubility in the system. The selected amine should also not be easily oxidized or contain groups that would inhibit generation of peracetic acid or degrade the peracetic acid after generation. Exemplary amines are listed below. Volatile amines are most preferred to obtain "no-rinse" formulations. The alkalinity source can be included in the acetyl donor and solvent portion or as a separate third component.

Example Alkalinity Sources for DAMA Based Formulations

| Name | CAS# |
|---|---|
| Anhydrous Ammonia | 7664-41-7 |
| Ammonium Hydroxide | 1336-21-6 |
| Triethylamine | 121-44-8 |
| Triethanolamine | 102-71-6 |
| 2-Ethanolamine | 141-43-5 |
| 2-(methylamino) ethanol | 109-83-1 |
| Diethanolamine | 111-42-2 |
| (R)-(−)-2-amino-1-butanol | 5856-63-3 |
| 2-(tert-butylamino) ethanol | 4620-70-6 |
| 2-(2-Aminoethylamino) ethanol | 111-41-1 |

Biodegradable chelating agents are also useful as an alkalinity source and include, by way of example, the tetrasodium salt of iminodisuccinic acid. Iminodisuccinic acid derivatives are preferred; however, other useful chelating agents include methylglycine diacetic acid (MGDA) and disodium ethylene diamine tetraacetic acid (EDTA).

Solvents are also used in the inventive formulations. Useful exemplary solvents for the TAED dispersion portion of the two-part liquid activator system include PPG-2 methyl ether and AMP-95 (2-amino-2-methyl-1-propanol). Other solvents useful with DAMA include isopropanol, ethyl lactate and Tergitol L-62 (also useful as a surfactant). Alternatively, DAMA based formulations may omit the solvent, if liquid DAMA is used.

The TAED dispersion typically includes a suspending agent such as magnesium aluminum silicate or Xanthan gum; however, other suspending agents known to those skilled in the art may be used.

All embodiments may further include adjuvants such as fragrances, dyes, colors or preservatives.

Table I below shows an exemplary formulation showing ranges for the components of the first embodiment.

TABLE I

| COMPONENTS | |
|---|---|
| Raw Material | Wt. % (range) |
| Dry TAED Activator | |
| Tetraacetylethylenediamine (TAED) | 50-85 |
| Dowfax C10L (alkyldiphenyloxide disulfonate) [1] | 10-30 |
| Baypure CX 100 (Iminodisuccinic acid, Tetrasodium salt) [2] | 1-15 |
| Sodium Carbonate [3] | 1-5 |
| Formulated Hydrogen Peroxide Solution | |
| Hydrogen Peroxide (35%) | 1-25 |
| Deionized Water | 70-98 |
| Poloxamer 407 [4] | 0.01-1.0 |
| Fragrance (Red Apple) | 0.01-1.0 |
| pH | 4.0-5.5 |

[1] Dowfax C10L is an anionic surfactant.
[2] Baypure CX 100 is a chelating agent and alkalinity source.
[3] Sodium carbonate is an alkalinity source
[4] Poloxamer 407 is a nonionic, PO/EO, block copolymer surfactant.

Table II below shows an exemplary formulation showing ranges for the components of the second embodiment.

TABLE II

| Raw Material | Wt. % (range) |
|---|---|
| TAED Dispersion | |
| Tetraacetylethylenediamine (TAED) | 30.4-40.0 |
| Deionized Water | 39-69 |
| Aluminum Magnesium (Suspending Agent) | 1.0-3.0 |
| PPG-2 Methyl Ether (Solvent) | 0-10 |
| Perlastan OCV (oleolyl sarcosinate) (Anionic Surfactant) | 0.5-2.0 |
| Glycacil-L (Iodo carbamato) (Preservative) | 0-0.5 |
| Glycolic Acid (pH adjuster/buffer) | 0-2.0 |
| pH | 3.5-6.5 |
| Alkaline Solution | |
| AMP-95 (2-amino-2-methyl-1-propanol) (Alkalinity Source/Solvent) | 4.20-7.0 |
| Dowfax C10L (alkyldiphenyloxide disulfonate) | 0-7.0 |
| Baypure CX 100 (Iminodisuccinic acid, Tetrasodium salt) | 0.84-4.2 |
| Deionized Water | 81.80-94.96 |
| pH | 11-12 |

TABLE II-continued

| Raw Material | Wt. % (range) |
|---|---|
| Formulated Hydrogen Peroxide Solution | |
| Hydrogen Peroxide (35%) | 1-25 |
| Deionized Water | 70-98 |
| Poloxamer 407 | 0.01-1.0 |
| Fragrance (Red Apple) | 0.01-1.0 |
| pH | 4.0-5.5 |

As discussed, the level concentration of peracetic acid generated varies depending on how much of the TAED activator is added to the hydrogen peroxide formulation. As stated, one mole of TAED generates two moles of peracetic acid. Generally, activator is added in quantities such that hydrogen peroxide will be in excess.

As an example, in the first embodiment, dry TAED activator may be combined with formulated hydrogen peroxide at the following ratio: 0.5-1.5 wt/wt of dry activator to 98.5-99.5% formulated hydrogen peroxide solution. This combination yields approximately 0.25% peracetic acid. As an example of the second embodiment, the TAED dispersion and alkaline solution are combined with the formulated hydrogen peroxide in the following ratio: 1-2 wt/wt TAED—dispersion; 1-2 wt/wt alkaline solution and 96-98% of formulated hydrogen peroxide solution. This combination also yields approximately 0.25% peracetic acid.

Figure 4:
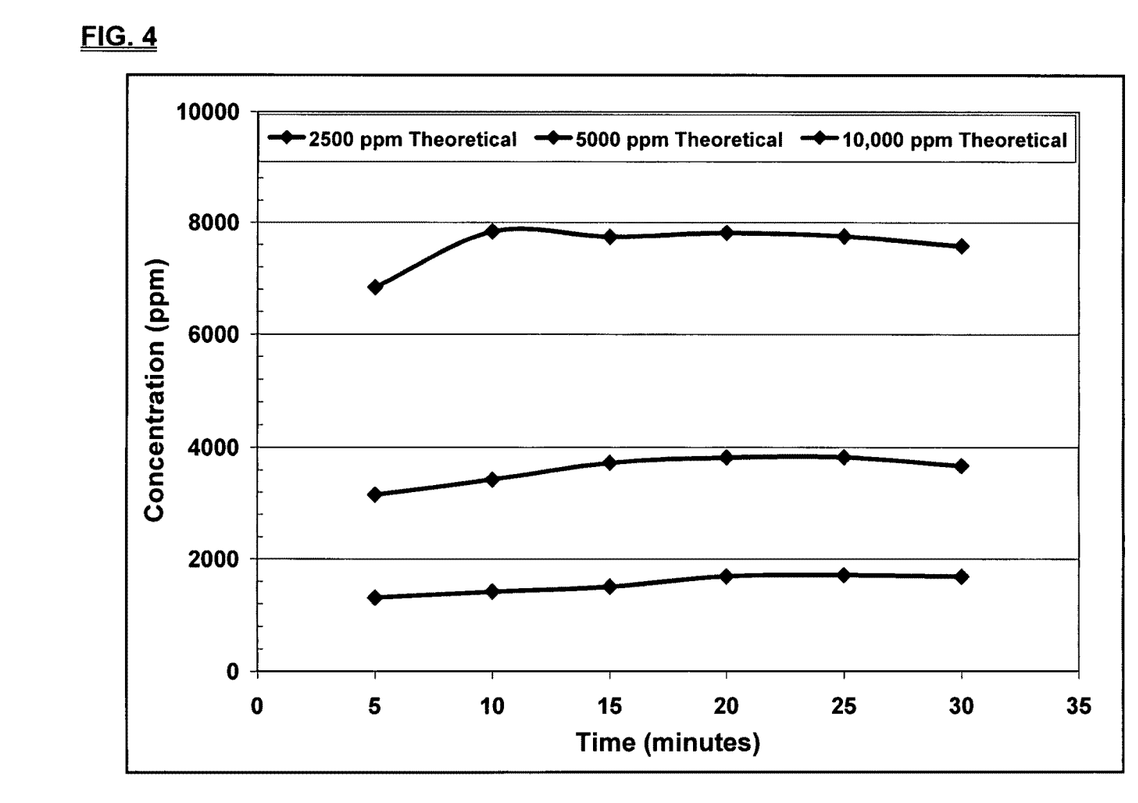
FIG. 4 is a graph which demonstrates the generation of peracetic acid from diacetylmethylamide, hydrogen peroxide, and ammonium hydroxide at three concentration levels monitored over time.

Tables III, IV and V below show exemplary formulations for the third embodiment comprising DAMA as the acetyl donor source for biological and chemical warfare agent testing. Table VI illustrates exemplary formulations for generating various concentrations of peracetic acid using DAMA as the acetyl donor. Concentrations of peracetic acid achieved are directly proportional to the concentration of DAMA in solution, as illustrated below in Table VI. The mixtures consistently produce levels of peracetic acid that are approximately 80% of what is calculated as theoretical. FIG. 4 demonstrates this at three levels of peracetic acid (2,500 ppm, 5,000 ppm, and 10,000 ppm) expected to be found in decontaminant products comprising DAMA, hydrogen peroxide and ammonium hydroxide.

TABLE III

Concentration of Ingredients in Sample Formulations used in Biological Efficacy Testing

| Ingredient | A | B | C | D |
|---|---|---|---|---|
| DAMA | 132 mM | 132 mM | 132 mM | 66 mM |
| $H_2O_2$ (wt. %)* | 9% | 9% | 9% | 4.5% |
| $NH_4OH$ Amine | 10 mM | 10 mM | 10 mM | 5 mM |

TABLE III-continued

Concentration of Ingredients in Sample Formulations used in Biological Efficacy Testing

| Ingredient | A | B | C | D |
|---|---|---|---|---|
| Solvent | Isopropanol 30% | Ethyl Lactate 30% | Tergitol L-62 0.3% | None |
| Water | Balance | Balance | Balance | Balance |

*Concentrations of hydrogen peroxide are end use.

TABLE IV

Concentration of Ingredients in Sample Formulations used in Chemical Efficacy Testing

| Ingredient | E | F | G | H | I |
|---|---|---|---|---|---|
| DAMA | 66 mM | 66 mM | 132 mM | 132 mM | 66 mM |
| $H_2O_2$ (wt. %)* | 4.5% | 4.5% | 4.5% | 4.5% | 4.5% |
| Amine | $NH_4OH$ 5 mM | $NH_4OH$ 5 mM | $NH_4OH$ 10 mM | Ethanolamine 6 mM | $NH_4OH$ 5 mM |
| Solvent | None | Isopropanol 30% | Isopropanol 30% | Isopropanol 30% | None |
| Add Ingredients | — | — | — | — | $NaHCO_3$ 0.1 M |
| Water | Balance | Balance | Balance | Balance | Balance |

*Concentrations of hydrogen peroxide are end use.

TABLE V

Concentration of Ingredients in Formulas Prepared with Different Amine Alkalinity Sources

| Ingredient | L | M | N |
|---|---|---|---|
| DAMA | 66 mM | 66 mM | 66 mM |
| $H_2O_2$ (wt. %)* | 4.5% | 4.5% | 4.5% |
| Amine | 2-(methylamino) ethanol 12.5 mM | (R)-(−)-2-Amino-1-Butanol 10.6 mM | 2-(tert-Butylamino) Ethanol 7.4 mM |
| Water | Balance | Balance | Balance |

*Concentrations of hydrogen peroxide are end use.

TABLE VI 2.4% Peracetic Acid Generating Formulas

| Alkalinity Source | DAMA (mL) | 7% $H_2O_2$ (mL) | 10% w/v $NH_4OH$ (mL) | 10% TEA (mL) | 2.0 M NH3 in IPA | $H_2O$ (mL) |
|---|---|---|---|---|---|---|
| 50 mM $NH_4OH$ | 0.432 | 6.500 | 0.175 | — | — | 2.893 |
| 70 mM TEA | 0.432 | 6.500 | — | 1.951 | — | 1.117 |
| 60 mM NH3 in IPA | 0.432 | 6.500 | — | — | 0.300 | 2.768 |
| 80 mM NH3 in IPA | 0.432 | 6.500 | — | — | 0.400 | 2.668 |

1.2% Peracetic Acid Generating Formulas

| Alkalinity Source | DAMA (mL) | 7% $H_2O_2$ (mL) | 10% w/v $NH_4OH$ (mL) | 10% TEA (mL) | $H_2O$ (mL) |
|---|---|---|---|---|---|
| 20 mM $NH_4OH$ | 0.216 | 6.500 | 0.070 | — | 3.214 |
| 30 mM $NH_4OH$ | 0.216 | 6.500 | 0.105 | — | 3.179 |
| 40 mM $NH_4OH$ | 0.216 | 6.500 | 0.140 | — | 3.144 |
| 60 mM TEA | 0.216 | 6.500 | — | 0.836 | 2.448 |

TABLE VI-continued

| | DAMA (mL) | DMF (mL) | 7% H₂O₂ (mL) | BI (g) | H₂O (mL) |
|---|---|---|---|---|---|
| 70 mM TEA | 0.216 | 6.500 | — | 0.975 | 2.309 |
| 80 mM TEA | 0.216 | 6.500 | — | 1.115 | 2.169 |

| 0.4% Peracetic Acid Generating Formula | | | | | |
|---|---|---|---|---|---|
| Alkalinity Source | DAMA (mL) | DMF (mL) | 7% H₂O₂ (mL) | BI (g) | H₂0 (mL) |
| 5% DMF + 90 mM Benzimidazole | 0.072 | 0.5 | 6.5 | 0.1065 | 2.780 |

IPA = isopropyl alcohol
BI = benzimidazole
DMF = dimethylformamide
DAMA = diacetylmethylamine
TEA = triethylamine The inventive compositions have application in a wide variety of uses. The inventive compositions are useful as disinfectants/sterilants to clean floors, countertops and other high-touch areas of hospitals or other health care institutions. They are also useful to clean various hard surfaces and equipment in pharmaceutical manufacturing facilities such as counters, floors, clean rooms, laboratories and hard surfaces in animal facilities.

EXAMPLES

Example 1

Efficacy

Figure 1:
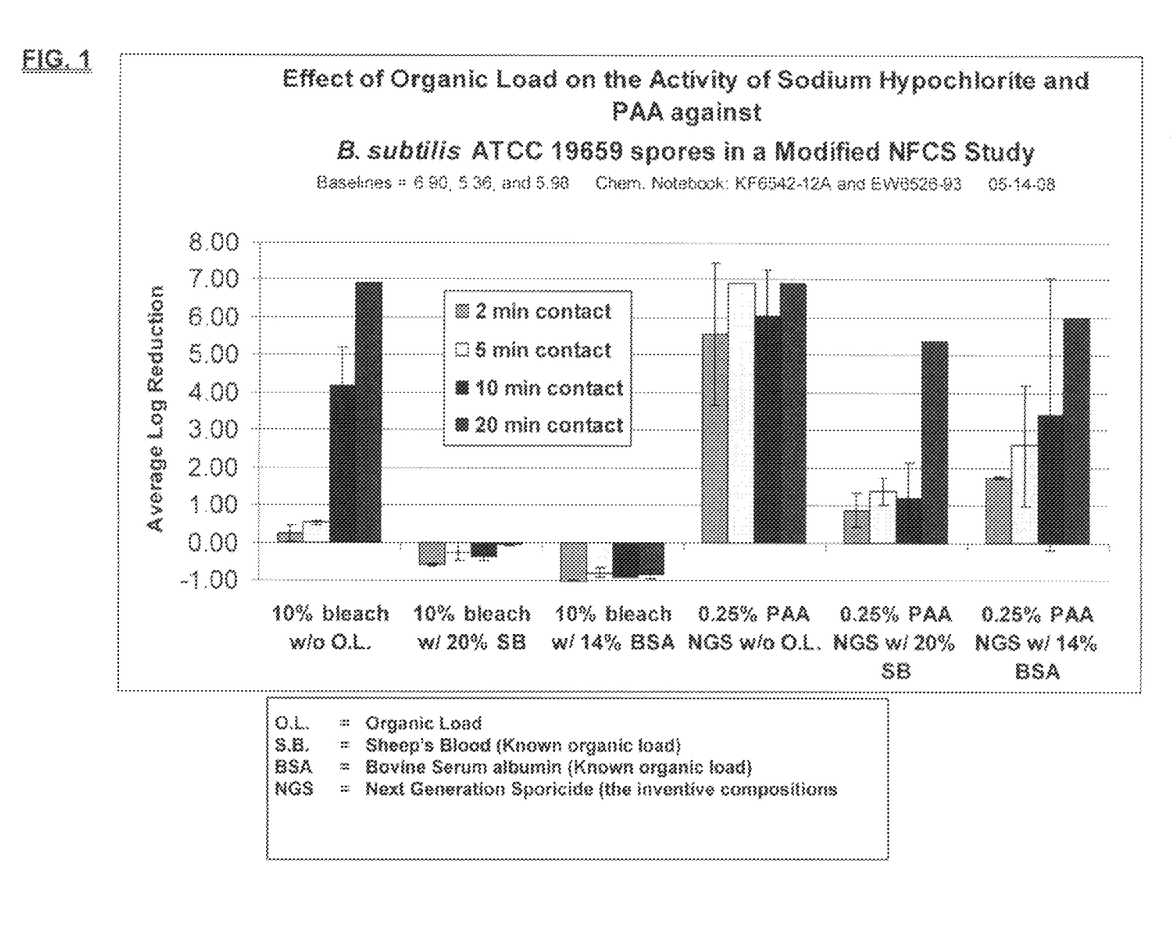
FIG. 1 is a graph which depicts superior sporicidal efficacy against Bacillus subtilis (in a modified Non-Food Contact Sanitizer Study) of the inventive formulation of approximately 0.25% peracetic acid as compared to a 1:10 dilution of bleach in water, in the presence of various organic loads and contact times of 2, 5, 10 and 20 minutes.

Sporicidal efficacy of the two-part liquid activator/formulated hydrogen peroxide system in a modified Non-Food Contact Sanitizer (NFCS) study is shown in FIG. 1. The results show that the inventive formulation, which generated approximately 0.25% peracetic acid, was superior to bleach (1:10 dilution in water) against *Bacillus subtilis*, a known spore former, in the presence of various organic loads and varying contact times. *Bacillus subtilis*, ATCC 19659 is useful as a surrogate for spore forming bacteria, such as anthrax, among others.

Example 2

Efficacy

Sporicidal efficacy of the inventive compositions was tested, using the Quantitative Carrier Test 2 (QCT-2) method against *C. diff* spores. The inventive composition shown in Table VII, below, was tested at various concentrations and mixed as indicated below.

TABLE VII

| Dry TAED Activator | | |
|---|---|---|
| Ingredient | Function | Amount (wt. %) |
| Tetraacetylethylenediamine (TAED) | Active Ingredient | 63.58% |
| Alkyldiphenyl Oxide Disulfonate (Dowfax C10L - 45% active (aq)) | Anionic Surfactant/ Dispersant | 11.49% |
| Tetrasodium Iminodisuccinate | Chelating Agent/ Alkalinity Source | 22.26% |
| Sodium Carbonate | Alkalinity Source/Buffer | 2.67% |

TABLE VII-continued

| Formulated Liquid Hydrogen Peroxide | | |
|---|---|---|
| Ingredient | Function | Concentration |
| 35% Hydrogen Peroxide (aq) | Active Ingredient | 2.86% |
| Deionized Water | — | 96.79% |
| Poloxamer 407 | Nonionic Surfactant | 0.05% |
| Fragrance | Fragrance | 0.30% |

Dilutions:
To generate 0.050% peracetic acid, 0.225 grams of the dry TAED activator was added to 200 mL of the formulated hydrogen peroxide.
To generate 0.075% peracetic acid, 0.337 grams of the dry TAED activator was added to 200 mL of the formulated hydrogen peroxide.
To generate 0.100% peracetic acid, 0.449 grams of the dry TAED activator was added to 200 mL of the formulated hydrogen peroxide.
To generate 0.125% peracetic acid, 0.562 grams of the dry TAED activator was added to 200 mL of the formulated hydrogen peroxide.
To generate 0.150% peracetic acid, 0.674 grams of the dry TAED activator was added to 200 mL of the formulated hydrogen peroxide.
To generate 0.175% peracetic acid, 0.786 grams of the dry TAED activator was added to 200 mL of the formulated hydrogen peroxide.
To generate 0.200% peracetic acid, 0.898 grams of the dry TAED activator was added to 200 mL of the formulated hydrogen peroxide.
To generate 0.250% peracetic acid, 1.123 grams of the dry TAED activator was added to 200 mL of the formulated hydrogen peroxide.

Figure 2:
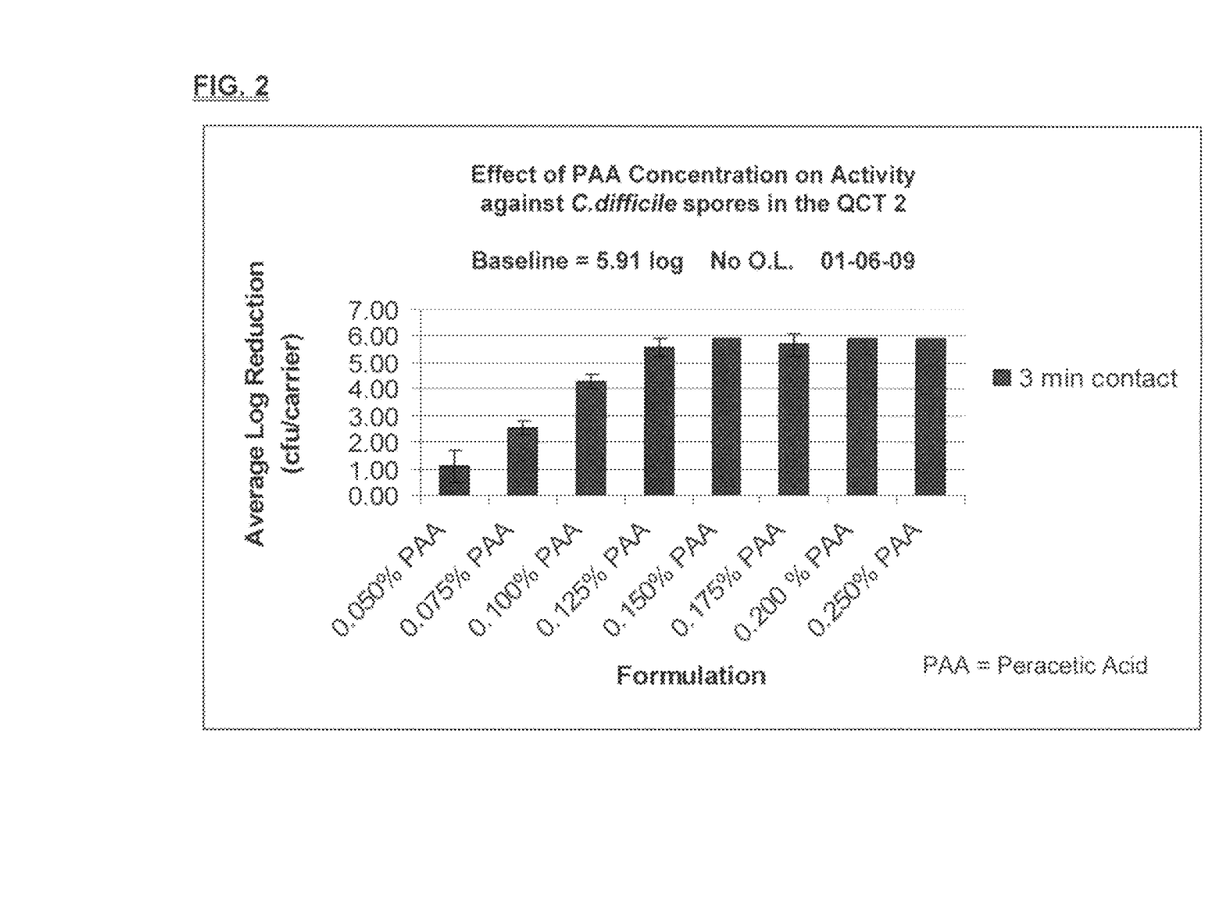
FIG. 2 is a bar graph which shows the effect of varying concentrations of peracetic acid (PAA) against C. difficile spores in a Quantitative Carrier Test 2 (QCT-2) for a three minute contact time.

PAA generated from the powdered activator/formulated liquid hydrogen peroxide system, at various use concentrations, is shown in FIG. 2. FIG. 2 shows average log reduction (cfu/carrier) for varying concentrations of PAA for a 3 minute contact time. Results reflect excellent activity against *C. diff* spores for peracetic acid levels of greater than 0.075% at 3 minute contact time. Efficacy was demonstrated by a log reduction of greater than 5.

Example 3

Effect of Soil Load

The effect of organic soil load on average log reduction using QCT-2 testing was also evaluated. The formulation used is set forth in Table VIII below.

TABLE VIII

| Dry TAED Activator | | |
|---|---|---|
| Ingredient | Function | Amount |
| Tetraacetylethylenediamine (TAED) | Active Ingredient | 0.2757 grams |
| Alkyldiphenyl Oxide Disulfonate (Dowfax C10L - 45% active (aq)) | Anionic Surfactant/ Dispersant | 0.0498 grams |
| Tetrasodium Iminodisuccinate | Chelating Agent/ Alkalinity Source | 0.1107 grams |
| Sodium Carbonate | Alkalinity Source/ Buffer | 0.0133 grams |

TABLE VIII-continued

Dry TAED Activator

| | | |
|---|---|---|
| Polyvinyl Alcohol Film* | Film Material | 0.0792 grams |

*PVA film was added to have the powder in a PVA water-soluble pouch that dissolves upon "activation." Studies have shown it had no impact on efficacy or peracetic acid generation.

Formulated Liquid Hydrogen Peroxide

| Ingredient | Function | Concentration (wt. %) |
|---|---|---|
| 35% Hydrogen Peroxide (aq) | Active Ingredient | 2.86% |
| Deionized Water | — | 96.79% |
| Poloxamer 407 | Nonionic Surfactant | 0.05% |
| Fragrance | Fragrance | 0.30% |

The above powder composition was added to 200 mL of the formulated hydrogen peroxide to form a solution containing about 0.075% PAA solution (~6% TAED).

Figure 3:
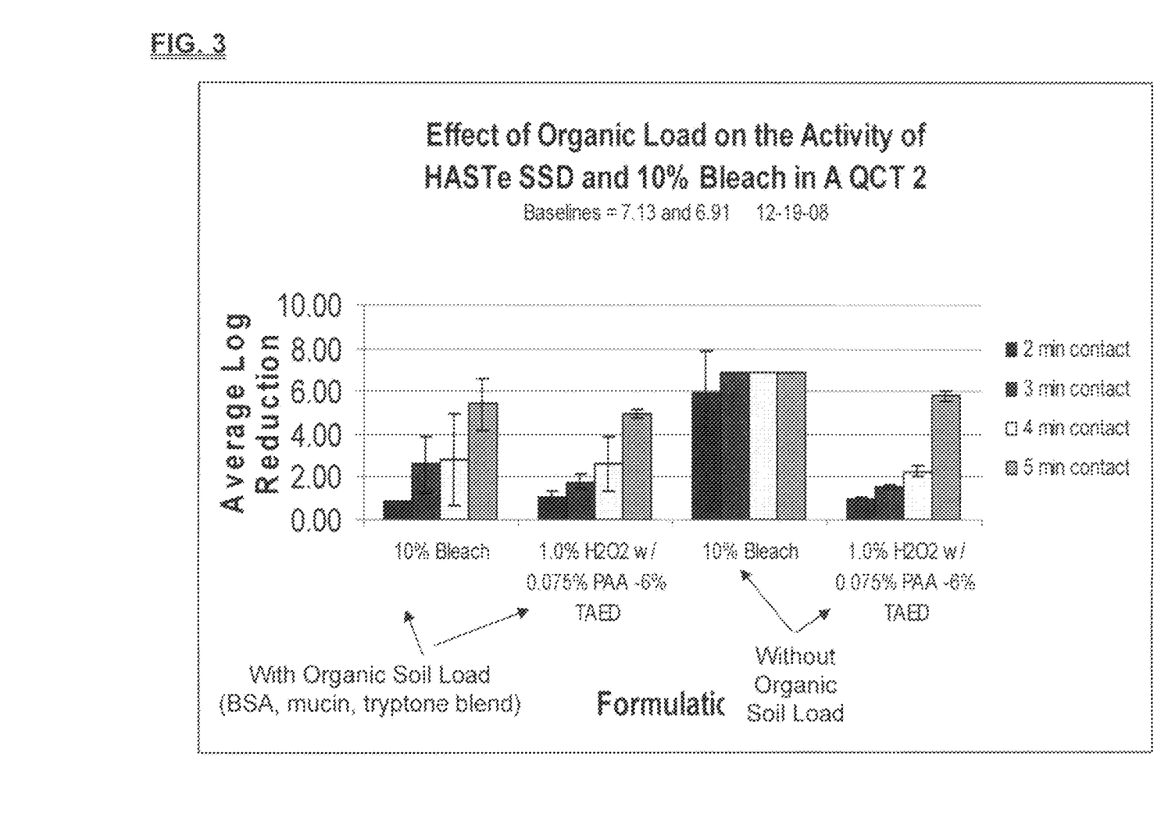
FIG. 3 is a bar graph which shows the effect of soil load on the inventive formulations versus a 10% bleach solution against C. difficile spores.

Sporicidal efficacy of the powdered activator/formulated liquid hydrogen peroxide system against *C. diff* spores was not affected by the presence of soil load. As seen in FIG. 3, sporicidal efficacy of a 10% bleach solution against *C. diff* spores was greatly affected, whereas the effect of soil load on the inventive formulations was minimal.

Example 4

Effect of DAMA Formulations on Spores

The example formulas presented above in Table III were evaluated for their effectiveness in decontaminating materials contaminated with bacterial spores. The formulas produced peracetic acid, known to be a highly effective bactericide/fungicide.

Figure 7:
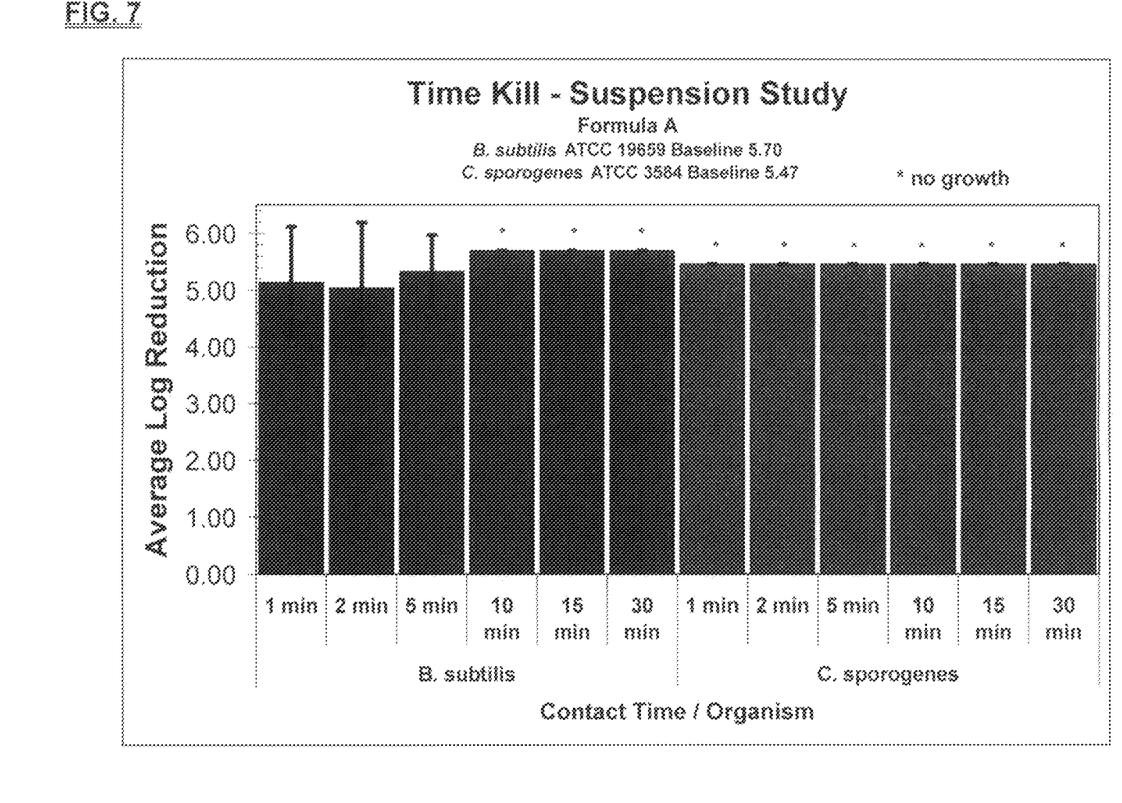
FIG. 7 is a bar graph showing equal efficacy of an inventive formulation against different types of spores.

Specifically, a study was conducted to compare Formula A's ability to kill *Bacillus subtilis* spores in comparison to *Clostridium sporogenes* spores (FIG. 7). The formula (see Table III) was found to be extremely effective in killing spores of both species.

Example 5

Effect of DAMA Formulation on Chemical Agents

Peracetic acid is a known decontaminant for Mustard (HD), Nerve (VX), and Soman (GD) chemical warfare agents. The results of using inventive formulas E-I (Table IV) with these agents are shown in Table IX. The formulas were reacted at a 50:1 decontaminant to agent ratio. The reaction progress was checked at 15 minutes and reported. The addition of a pH modifier in Formula 1 was able to increase the Soman (GD) activity.

TABLE IX

Efficacy of the Formulas Described in Table IV against Chemical Warfare Agents

| Formula | GD | HD | VX |
|---|---|---|---|
| E | 16.2% | 99.89% | 48% |
| F | <1.0% | 99.03% | 46% |
| G | 16.7% | 100.00% | 46% |
| H | 6.9% | 99.80% | 43% |
| I | 84.5% | 55.95% | 54% |

Example 6

Comparative Studies

Figure 5:
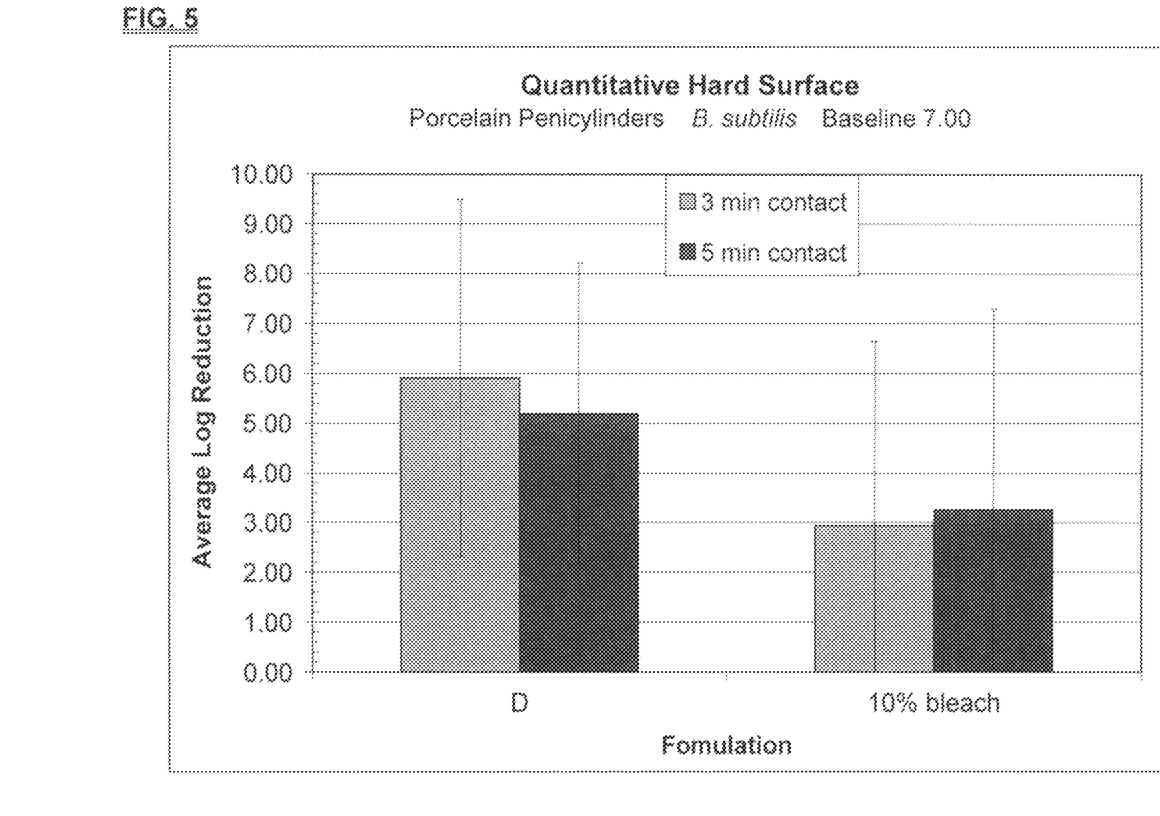
FIG. 5 is a bar graph comparing the hard surface biological efficacy of an inventive formulation as compared to 10% bleach.

A hard surface biological efficacy test was conducted on porcelain penicylinders in order to compare its efficacy to 10% household bleach (0.5% active). Formula D (Table III) was found to be at least as effective as bleach (FIG. 5).

Figure 6:
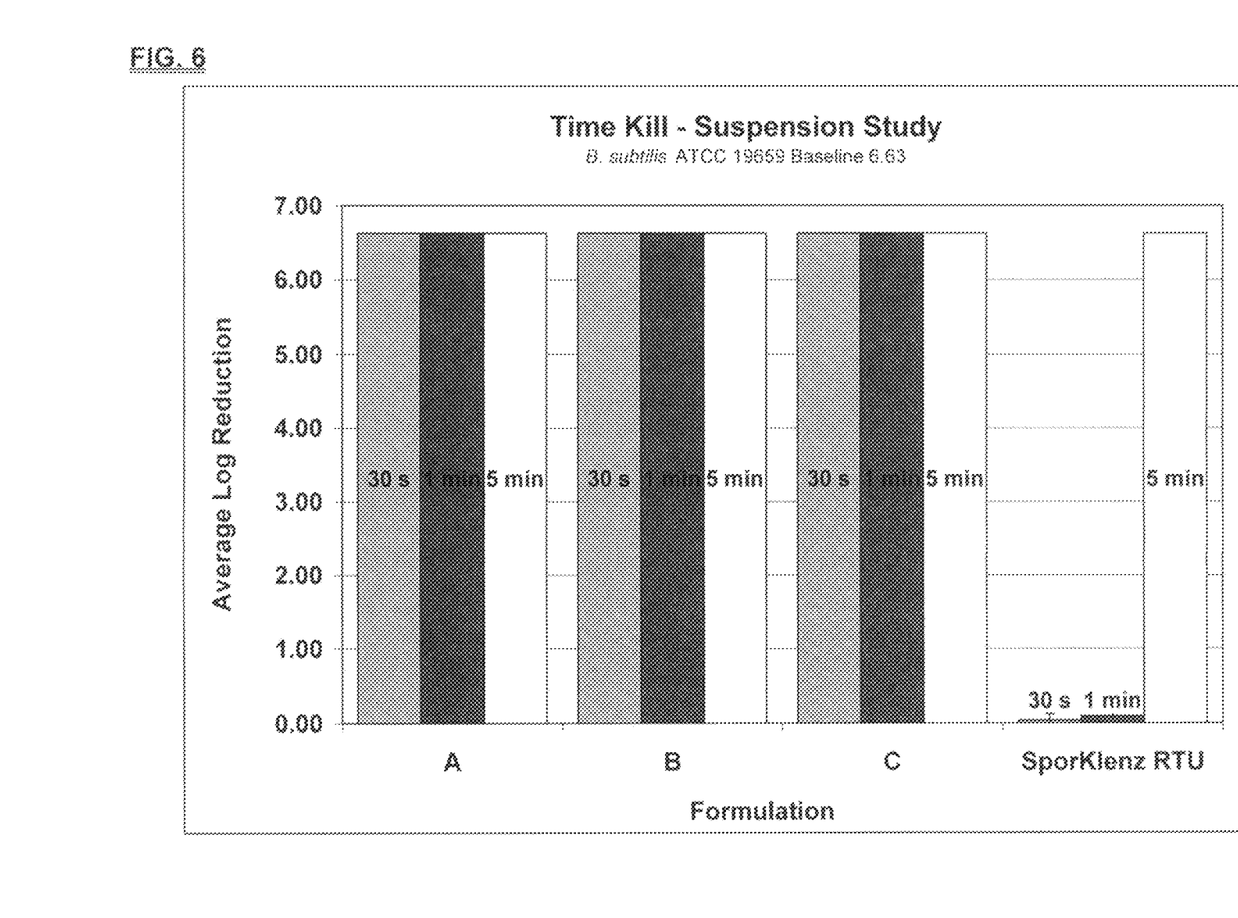
FIG. 6 is a bar graph comparing the biological efficacy of inventive formulations to a commercially available sporicide, wherein the inventive formulations demonstrated superior efficacy.

Several formulas were tested for their ability to kill bacterial spores as compared to a current commercially available sporicide (FIG. 6). Suspension studies were used to compare Formulations A, B and C (from Table III) to Spor-Klenz Ready-To-Use Cold Sterilant. Spor-Klenz is a product of STERIS Corporation and is currently one of the most effective sporicides on the market. All of the inventive formulations were found to be capable of demonstrating a 6.5 log reduction in *B. subtilis* spores in 30 seconds, and yielded superior results as compared to the Spor-Klenz.

In accordance with the patent statutes, the best mode and preferred embodiment have been set forth; the scope of the invention is not limited thereto, but rather by the scope of the attached claims.

What is claimed is:

1. A ready-to-use, multi-part composition that, upon combining the parts, generates, in situ, a low odor, neutral aqueous peracetic acid solution for use in decontaminating or disinfecting biological or chemical warfare agents, including spores, on hard surfaces, consisting essentially of:
   a. as a first part, an acetyl donor consisting of liquid diacetylmethylamine (DAMA);
   b. as a second part, a hydrogen peroxide solution, wherein the concentration of hydrogen peroxide is present in amounts less than about 10 weight percent;
   c. an alkalinity source included as a third part or combined with the first part, wherein the alkalinity source is selected from the group consisting of an anhydrous ammonia, ammonium hydroxide, triethylamine, triethanolamine, ethanolamine, diethanolamine, 2-(methylamino) ethanol, R-(−)-2-amino-1-butanol, 2(tert-butylamino) ethanol, or 2-(2-amino ethylamino) ethanol, and mixtures thereof;
   d. optionally, a low-foaming surfactant included in the first part; and
   e. water;
   wherein the composition is without the presence of detersive surfactants, enzymes, builders, foaming agents, anti-gel additives, or viscosity control agents, wherein the liquid acetyl donor, hydrogen peroxide solution and alkalinity source are mixed together just prior to use to form the peracetic acid solution, and wherein the peracetic acid solution requires no or less rinsing than other conventional decontamination or disinfecting compositions.

2. The composition as set forth in claim 1, wherein the optional low-foaming surfactant is n-oleoyl sarcosinate, alkyldiphenyl oxide disulfonate, or dodecylbenzene sulfonic acid, or combinations thereof.

3. The composition as set forth in claim 1, wherein the optional low-foaming surfactant is polyoxyethylene sorbitan monolaurate.

4. The composition as set forth in claim 1, further consisting essentially of a buffer.

5. A ready-to-use, multi-part composition that, upon combining the parts, generates, in situ, a low odor, neutral aqueous solution of peracetic acid for use in decontaminating or disinfecting biological or chemical warfare agents, including spores, on hard surfaces, consisting of:

a. as a first part, an acetyl donor consisting of diacetylmethylamine (DAMA) dispersed in a solvent;
b. a second part, an aqueous hydrogen peroxide solution, wherein the concentration of hydrogen peroxide is present in amounts less than about 10 weight percent;
c. an amine alkalinity source as a third part or in combination with the first part; and
d. water.

6. The composition as set forth in claim 5, wherein the solvent is isopropanol, ethyl lactate, or an ethylene oxide/propylene oxide copolymer, or combinations thereof.

7. The composition as set forth in claim 5, wherein the amine alkalinity source is ammonium hydroxide, ethanolamine, 2-(methylamino)ethanol, R-(−)-2-amino-1-butanol, or 2-(tert-butylamino) ethanol.

8. A composition for generating, in situ, a low odor, neutral aqueous solution of peracetic acid, useful for decontaminating or disinfecting biological or chemical warfare agents, including spores, on hard surfaces, consisting of:
a. diacetylmethylamine (DAMA) present in an amount ranging from about 0.5 up to about 10 wt. % of the total weight of components;
b. ammonium hydroxide present in an amount ranging from about 0.01 to about 1 wt. % of the total weight of components;
c. a solvent consisting of isopropanol, ethyl acetate or an ethylene oxide/propylene oxide copolymer, present in an amount ranging from about 0.3 to about 30 wt. % of the total weight of components;
d. a hydrogen peroxide solution, wherein the concentration of hydrogen peroxide is present in amounts less than about 10 weight percent; and
d. water.

9. A ready-to-use, multi-part composition that, upon combining the parts, generates, in situ, a low odor, neutral aqueous peracetic acid solution for use in decontaminating or disinfecting biological or chemical warfare agents, including spores, on hard surfaces, consisting of:
a. as a first part, an acetyl donor consisting of liquid diacetylmethylamine (DAMA);
b. as a second part, a hydrogen peroxide solution, wherein the concentration of hydrogen peroxide is present in amounts less than about 10 weight percent;
c. an alkalinity source included as a third part or combined with the first part, wherein the alkalinity source is selected from the group consisting of an anhydrous ammonia, ammonium hydroxide, triethylamine, triethanolamine, ethanolamine, diethanolamine, 2-(methylamino) ethanol, R-(−)-2-amino-1-butanol, 2(tert-butylamino) ethanol, or 2-(2-amino ethylamino) ethanol, and mixtures thereof;
d. a low-foaming surfactant included in the first part;
e. a buffer; and
e. water,
wherein the composition is without the presence of detersive surfactants, enzymes, builders, foaming agents, anti-gel additives, or viscosity control agents, wherein the liquid acetyl donor, hydrogen peroxide solution and alkalinity source are mixed together just prior to use to form the peracetic acid solution, and wherein the peracetic acid solution requires no or less rinsing than other conventional decontamination or disinfecting compositions.

10. A ready-to-use, multi-part composition that, upon combining the parts, generates, in situ, a low odor, neutral aqueous peracetic acid solution for use in decontaminating or disinfecting biological or chemical warfare agents, including spores, on hard surfaces, consisting of:
a. as a first part, an acetyl donor consisting of diacetylmethylamine (DAMA) dispersed in a solvent, wherein the solvent consists of isopropanol, ethyl acetate or an ethylene oxide/propylene oxide copolymer, present in an amount ranging from about 0.3 to about 30 wt. % of the total weight of components of the composition;
b. as a second part, a hydrogen peroxide solution, wherein the concentration of hydrogen peroxide is present in amounts less than about 10 weight percent;
c. an alkalinity source included as a third part or combined with the first part, wherein the alkalinity source is selected from the group consisting of an anhydrous ammonia, ammonium hydroxide, triethylamine, triethanolamine, ethanolamine, diethanolamine, 2-(methylamino) ethanol, R-(−)-2-amino-1-butanol, 2(tert-butylamino) ethanol, or 2-(2-amino ethylamino) ethanol, and mixtures thereof;
d. a low-foaming surfactant included in the first part;
e. a buffer; and
e. water,
wherein the composition is without the presence of detersive surfactants, enzymes, builders, foaming agents, anti-gel additives, or viscosity control agents, wherein the liquid acetyl donor, hydrogen peroxide solution and alkalinity source are mixed together just prior to use to form the peracetic acid solution, and wherein the peracetic acid solution requires no or less rinsing than other conventional decontamination or disinfecting compositions.

* * * * *